(12) United States Patent
Chang et al.

(10) Patent No.: US 8,722,922 B2
(45) Date of Patent: May 13, 2014

(54) PROCESS FOR HYDROGENATION OF POLYCARBOXYLIC ACIDS OR DERIVATIVES THEROF

(75) Inventors: Hsu-Kai Chang, Hsinchu (TW);
Chion-Hwang Lee, Hsinchu (TW);
Kuo-Ching Wu, Hsinchu (TW);
Hsi-Yen Hsu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 88 days.

(21) Appl. No.: 13/465,232

(22) Filed: May 7, 2012

(65) Prior Publication Data
US 2013/0150614 A1    Jun. 13, 2013

(30) Foreign Application Priority Data

Dec. 12, 2011   (TW) .............................. 100145727 A

(51) Int. Cl.
*C07C 67/303* (2006.01)
(52) U.S. Cl.
USPC ........................................ 560/127; 562/509
(58) Field of Classification Search
None
See application file for complete search history.

(56) References Cited

U.S. PATENT DOCUMENTS

| | | | |
|---|---|---|---|
| 3,027,398 A | 3/1962 | Foohey et al. | |
| 5,286,898 A | 2/1994 | Gustafson et al. | |
| 5,319,129 A | 6/1994 | Gustafson et al. | |
| 6,284,917 B1 | 9/2001 | Brunner et al. | |
| 6,740,773 B2 | 5/2004 | Bohnen et al. | |
| 6,888,021 B2 | 5/2005 | Brunner et al. | |
| 6,927,306 B2 | 8/2005 | Zaima | |
| 7,361,714 B2 | 4/2008 | Grass et al. | |
| 7,498,450 B2 | 3/2009 | Wood et al. | |
| 7,595,420 B2 | 9/2009 | Schlosberg et al. | |
| 7,632,961 B2 | 12/2009 | Bueschken et al. | |
| 7,683,204 B2 | 3/2010 | Bueschken et al. | |
| 7,893,295 B2 * | 2/2011 | Schlosberg et al. | 560/127 |
| 2005/0038285 A1 | 2/2005 | Maschmeyer et al. | |
| 2006/0041167 A1 * | 2/2006 | Grass et al. | 562/509 |
| 2008/0146832 A1 * | 6/2008 | Grass et al. | 560/127 |
| 2011/0196171 A1 | 8/2011 | Sugawara | |
| 2013/0029831 A1 | 1/2013 | Kilner et al. | |

FOREIGN PATENT DOCUMENTS

| | | |
|---|---|---|
| CN | 1380282 | 11/2002 |
| JP | 2006-083080 A | 3/2006 |
| TW | I1243188 | 11/2002 |
| TW | I259177 | 8/2006 |
| TW | I265332 | 11/2006 |
| TW | I273101 B | 2/2007 |
| TW | I306412 B | 2/2009 |
| TW | 201008907 A1 | 3/2010 |
| TW | I351314 B | 11/2011 |

OTHER PUBLICATIONS

Taiwan Office Action for Taiwan Application No. 100145727 dated Sep. 4, 2013.

* cited by examiner

*Primary Examiner* — Brian J Davis
(74) *Attorney, Agent, or Firm* — Muncy, Geissler, Olds & Lowe, P.C.

(57) ABSTRACT

The disclosure provides a process for hydrogenation of polycarboxylic acids or derivatives thereof, including: hydrogenation of polycarboxylic acids or derivatives thereof in the presence of a catalyst, wherein the catalyst includes an active metal and a support, the support includes a Group IIA element and a Group IIIA element, and the active metal includes a Group VIIIB element.

14 Claims, 2 Drawing Sheets

PROCESS FOR HYDROGENATION OF POLYCARBOXYLIC ACIDS OR DERIVATIVES THEROF

CROSS REFERENCE TO RELATED APPLICATIONS

This application claims priority of Taiwan Patent Application No. 100145727, filed on Dec. 12, 2011, the entirety of which is incorporated by reference herein.

BACKGROUND

1. Field of the Disclosure

The present disclosure relates to a hydrogenation process, and in particular relates to a process for hydrogenation of polycarboxylic acids or derivatives thereof.

2. Description of the Related Art

A hydrogenation reaction is a common reaction found in the petrochemical industry. A catalyst is usually used in a hydrogenation reaction and it mainly comprises transition metal elements. The hydrogenation products of polycarboxylic acids or derivatives thereof have several uses, such as being used as a plasticizer of polymer materials or additives of metal processing.

In various plasticizers, the amount of dioctyl phthalate (DOP) needed is large, and it adversely affects human beings and the environment. Thus, other substitutes have been developed, such as 1,2-cyclohexane polycarboxylic acid esters.

1,2-cyclohexane polycarboxylic acid esters are obtained by a simple process for hydrogenation of polycarboxylic acids or derivatives thereof. There are several hydrogenation processes disclosed. However, the conventional hydrogenation processes must be carried out at a high pressure (about 50-200 Bar), and high-pressure hydrogen is additionally provided to increase the hydrogenation yield of the hydrogenation processes to more than 90%. Thus, the equipment costs of the hydrogenation process is expensive making fabrication costs high.

Accordingly, there is a need to develop a process for hydrogenation of polycarboxylic acids or derivatives thereof. The hydrogenation process may be carried out in a relatively low pressure environment and have a high hydrogenation yield, thus, fabrication costs are lower than the conventional processes.

BRIEF SUMMARY

The disclosure provides a process for hydrogenation of polycarboxylic acids or derivatives thereof, comprising: hydrogenation of polycarboxylic acids or derivatives thereof in the presence of a catalyst, wherein the catalyst comprise an active metal and a support, the support comprises a Group IIA element and a Group IIIA element, and the active metal comprises a Group VIIIB element.

A detailed description is given in the following embodiments with reference to the accompanying drawings.

BRIEF DESCRIPTION OF THE DRAWING

For a more complete understanding of the present disclosure, and the advantages thereof, reference is now made to the following descriptions taken in conjunction with the accompanying drawings, in which.

DETAILED DESCRIPTION

Figure 1A:
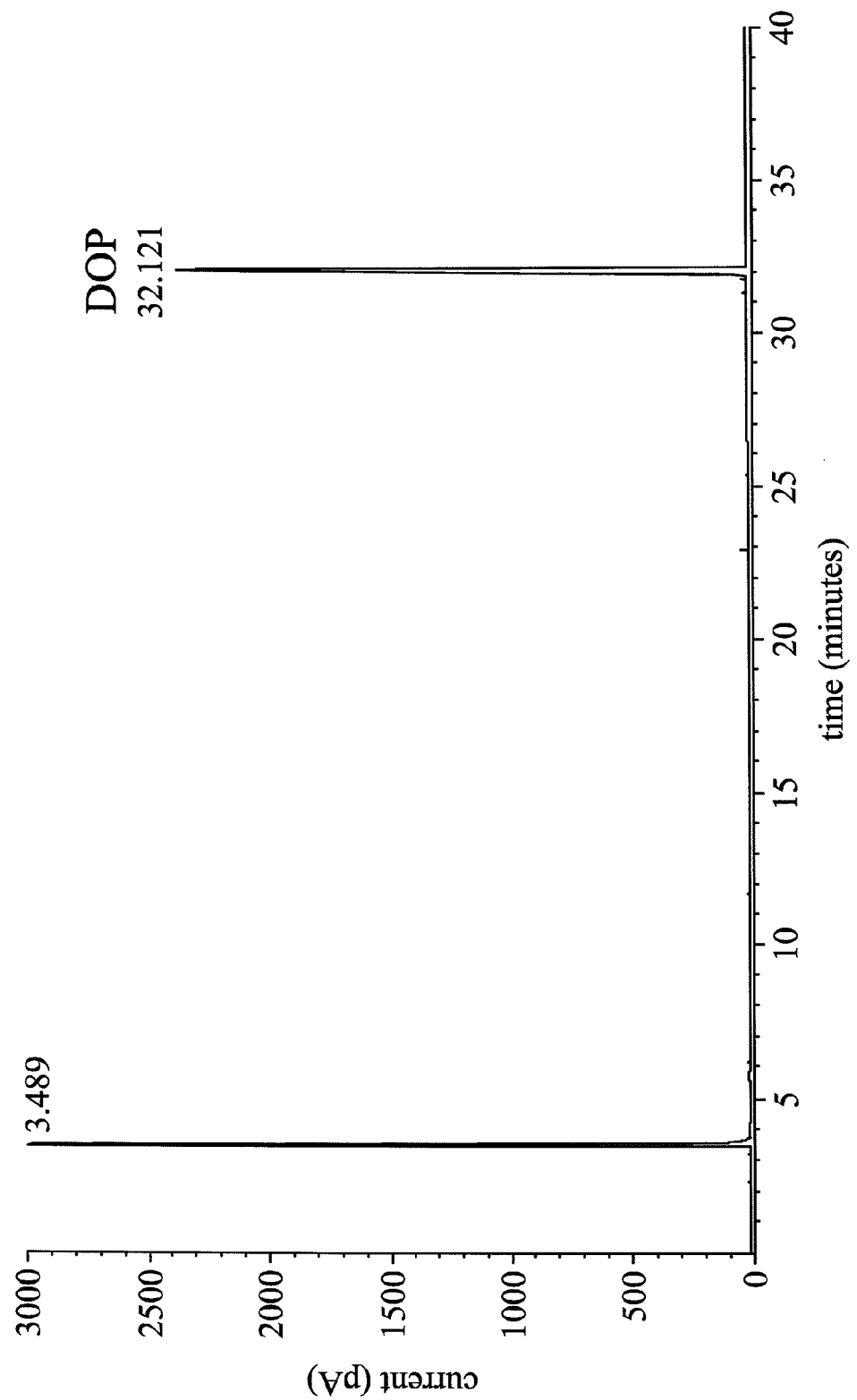
FIGS. 1A-1B show the diagrams of the gas chromatography (GC) of the polycarboxylic acids in accordance with an embodiment of the disclosure.

The following description is of the best-contemplated mode of carrying out the disclosure. This description is made for the purpose of illustrating the general principles of the disclosure and should not be taken in a limiting sense. The scope of the disclosure is best determined by reference to the appended claims.

The disclosure provides a process for hydrogenation of polycarboxylic acids or derivatives thereof. The process comprises the following steps. Firstly, the polycarboxylic acids or derivatives thereof are provided. The polycarboxylic acids comprise phthalic acid, terephthalic acid, isophthalic acid, trimellitic acid, trimesic acid, hemimellitic acid or pyromellitic acid.

The polycarboxylic acid derivatives comprise the monoester, diester, trimester, tetreaester or anhydride of the polycarboxylic acids. The ester comprises $C_1$-$C_{30}$ alkyl ester, $C_3$-$C_{30}$ cycloalkyl ester or $C_1$-$C_{30}$ alkoxyalkyl ester, preferably $C_2$-$C_{20}$ alkyl ester, $C_3$-$C_{20}$ cycloalkyl ester or $C_2$-$C_{20}$ alkoxyalkyl ester, and the alkyl may be linear or branched.

The polycarboxylic acid derivatives comprise monomethyl phthalate, dimethyl phthalate, di-n-propyl phthalate, di-n-butyl phthalate, diisobutyl phthalate, di-tert-butyl phthalate, monoglycol phthalate, diglycol phthalate, di-n-octyl phthalate, diisooctyl phthalate, di-2-ethylhexyl phthalate, di-n-nonyl phthalate, diisononyl phthalate, di-n-decyl phthalate, di-2-propylheptyl phthalate, diisodecyl phthalate, di-n-undecyl phthalate, diisoundecyl phthalate, ditridecyl phthalate, di-n-octadecyl phthalate, diisooctadecyl phthalate, monomethyl isophthalate, dimethyl isophthalate, diethyl isophthalate, di-n-propyl isophthalate, di-n-butyl isophthalate, diisobutyl isophthalate, di-tert-butyl isophthalate, monoglycol isophthalate, diglycol isophthalate, di-n-octyl isophthalate, diisooctyl isophthalate, diisononyl isophthalate, di-n-decyl isophthalate, diisodecyl isophthalate, di-n-undecyl isophthalate, ditridecyl isophthalate, diisooctadecyl isophthalate, monomethyl terephthalate, dimethyl terephthalate, diethyl terephthalate, di-n-propyl terephthalate, dibutyl terephthalate, diisobutyl terephthalate, di-tert-butyl terephthalate, monoglycol terephthalate, diglycol terephthalate, n-octyl terephthalate, diisooctyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisododecyl terephthalate, ditridecyl terephthalate, di-n-octadecyl terephthalate or diisooctadecyl terephthalate.

In one embodiment, the polycarboxylic acid derivative is diethyl phthalate (DEP).

In another embodiment, the polycarboxylic acid derivative is dibutyl phthalate (DBP).

In yet another embodiment, the polycarboxylic acid derivative is diisooctyl phthalate (DOP).

In another embodiment, the polycarboxylic acid derivative is diisononyl phthalate (DINP).

Then, a process for hydrogenation of polycarboxylic acids or derivatives thereof is carried out in a reactor. The reactor comprises a continuous reactor (such as trickle bed reactor) or non-continuous reactor (such as batchwise reactor).

The reactor is conducted in a normal pressure or a pressure of about 1-50 Bar, preferably about 1-20 Bar, and more preferably about 1-10 Bar. The reactor is conducted at temperature of about 100-250° C., and preferably about 150-220° C.

The polycarboxylic acids or derivatives thereof are hydrogenated in the presence of a catalyst, and the catalyst comprises an active metal and a support, the support comprises a Group IIA element and a Group IIIA element, the Group IIA element comprises Mg, Ca, Sr, Ba or combinations thereof, and the Group IIIA element comprises B, Al or combinations thereof.

The active metal comprises a Group VIIIB element, and the Group VIIIB element comprises Pt, Pd, Ru, Rh or combinations thereof. The active metal comprises 0.2-10 weight % of the catalyst, and preferably 0.2-3 weight %, and more preferably 0.2-1.5 weight %.

Additionally, the catalyst further comprises an additive which comprises activated carbon, silicon carbide, aluminum oxide, silicon dioxide, titanium dioxide or combinations thereof.

Furthermore, a forming agent may be added into the catalyst. The forming agent is such as alumina sol, silica gel, titanium sol, zirconium sol or pitch. The function of the forming agent is to mold the shape (such as columnar shape) of the catalyst.

In one embodiment, the aluminum oxide powder and the calcium oxide powder are mixed to form a support. An active metal palladium chloride ($PdCl_2$) is added into the support to form a catalyst. The diethyl cyclohexane-1,2-dicarboxylate is obtained by hydrogenating of the diethyl phthalate (DEP) in the presence of the catalyst.

In another embodiment, the magnesium nitrate and the aluminum nitrate are precipitated by adding the sodium hydroxide (NaOH) and the sodium carbonate ($Na_2CO_3$) to form a support. An active metal palladium chloride ($PdCl_2$) is added into the support to form a catalyst. The dioctyl cyclohexane-1,2-dicarboxylate is obtained by hydrogenating of the dioctyl phthalate (DOP) in the presence of the catalyst.

In yet another embodiment, the magnesium nitrate and the aluminum nitrate are precipitated by adding the sodium hydroxide (NaOH) and the sodium carbonate ($Na_2CO_3$), and the additive aluminum oxide is added to the above mixture to form a support. An active metal palladium chloride ($PdCl_2$) is added into the support to form a catalyst. The diisononyl cyclohexane-1,2-dicarboxylate is obtained by hydrogenating of the diisononyl phthalate (DINP) in the presence of the catalyst.

Additionally, a solvent may be added into the reactor to increase the solubility of the polycarboxylic acids or derivatives thereof. Alternatively, a solvent may not be added into the reactor to avoid the problem of solvent removal.

In the prior art, the hydrogenation process is carried out at a high pressure (about 50-200 Bar). Compared with prior art, the hydrogenation process of polycarboxylic acids or derivatives thereof is carried out at a normal pressure or a relatively lower pressure (smaller than about 50 Bar). Additionally, the process of the disclosure has a high hydrogenation yield larger than 99%, and thus fabrication costs are lower.

FABRICATION EXAMPLE

Fabrication Example 1

Fabrication of Catalyst A 100 g of activated aluminum oxide, 30 g of the calcium oxide were added in 200 ml of de-ionized water to form a slurry. The slurry was stirred for 1 hour and then dried at 120° C., and then calcined at 450° C. for 6 hours to form a powder.

50 g of the power obtained by the above step and 50 ml of the palladium chloride solution ($PdCl_2$) containing 0.35 g of palladium were mixed and then dried at 120° C. The dried powder was molded to obtain the uniform particles with 20-30 mesh size. Then, the molded particles were calcined at 450° C. for 4 hours to obtain the catalyst A.

Before performing a hydrogenation process, the catalyst A was filled into a reaction column and then was pretreated in a hydrogen atmosphere for 4 hours.

Fabrication Example 2

Fabrication of Catalyst B 140 g of magnesium nitrate ($Mg(NO_3)_2 \cdot 6H_2O$), and 155 g of the aluminum nitrate ($Al(NO_3)_3 \cdot 9H_2O$) were dissolved in 2000 ml of de-ionized water to form a solution. The sodium hydroxide (NaOH) and sodium carbonate ($Na_2CO_3$) with a weight ratio of 70:130 were dissolved in 1100 ml of de-ionized water to from a base solution. The base solution was added into the solution and stirred at 60-80° C. The mixed solution was filtered to obtain a filter cake. The filter cake was washed by water and then dried at 110° C.

40 g of the power obtained by the above step and 50 ml of the palladium chloride solution ($PdCl_2$) containing 0.4 g of palladium were mixed and then dried by heating. The dried powder was molded to obtain the uniform particles with 20-30 mesh size. Then, the molded particles were calcined at 450° C. for 4 hours to obtain the catalyst B.

Before performing a hydrogenation process, the catalyst B was filled into a reaction column and was pretreated in a hydrogen atmosphere for 4 hours.

Fabrication Example 3

Fabrication of Catalyst C 140 g of magnesium nitrate ($Mg(NO_3)_2 \cdot 6H_2O$), and 155 g of the aluminum nitrate ($Al(NO_3)_3 \cdot 9H_2O$) were dissolved in 2000 ml of de-ionized water to form a solution. The sodium hydroxide (NaOH) and sodium carbonate ($Na_2CO_3$) with a weight ratio of 70:130 were dissolved in 1100 ml of de-ionized water to from a base solution. The base solution was added into the solution and stirred at 60-80° C. Then, 100 g of aluminum oxide was added into the mixed solution and stirred for 1 hour. The mixed solution was filtered to obtain a filter cake. The filter cake was washed by water and then dried at 110° C.

100 g of the power obtained by the above step, 20 g of the forming agent and adhesion agent were mixed and molded to form a support with a cylindrical shape. The molded support was calcined at 450° C. for 4 hours.

Next, the 100 g of cylindrical support and 200 ml of palladium chloride solution ($PdCl_2$) containing 1 g of palladium were mixed and then dried. The mixture were dried by heating and calcined at 450° C. for 4 hours to obtain the catalyst C with 20-30 mesh size.

Before performing a hydrogenation process, the catalyst C was filled into a reaction column and was pretreated in a hydrogen atmosphere for 4 hours.

EXAMPLE

Example 1

Scheme 1

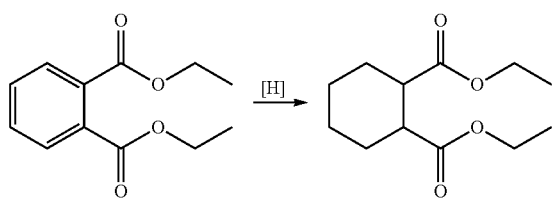

6 ml of catalyst A was placed in a fixed bed reactor (such as trickle bed reactor). A process for hydrogenation of the diethyl phthalate (DEP) was carried out in the trickle bed reactor according to scheme 1.

Hydrogenation reaction condition: at a normal pressure, the ethanol was used as a solvent, and the diethyl phthalate (DEP) and solvent were supplied at a ratio of 1:1. The supply rate of the hydrogen was about 70 mL/min, the reaction temperature was about 200° C., and reaction flow rate was about 1.0 mL/hr. About 100% of hydrogenation yield was shown, following analysis by a gas chromatography (GC) at the normal pressure.

Example 2

Scheme 2

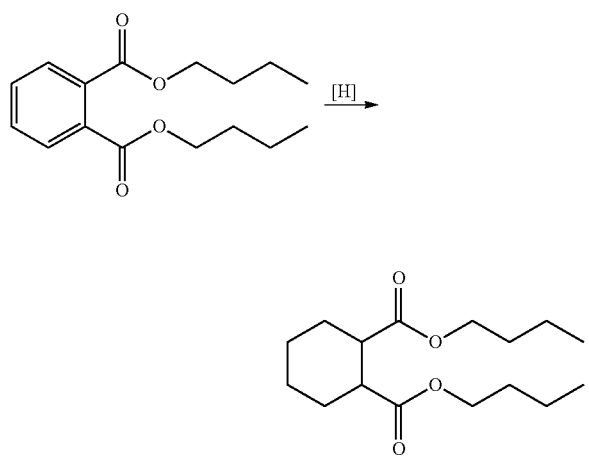

6 ml of catalyst A was placed in a fixed bed reactor (such as trickle bed reactor). A process for hydrogenation of the dibutyl phthalate (DBP) was carried out in the trickle bed reactor according to scheme 2.

Hydrogenation reaction condition: at a normal pressure, the n-butanol was used as a solvent, and the dibutyl phthalate (DBP) and the solvent were supplied at a ratio of 1:1. The supply rate of the hydrogen was about 35 mL/min, the reaction temperature was about 200° C., and the reaction flow rate was about 1.0 mL/hr. About 100% of hydrogenation yield was shown, following analysis by a gas chromatography (GC) at the normal pressure.

Example 3

Scheme 3

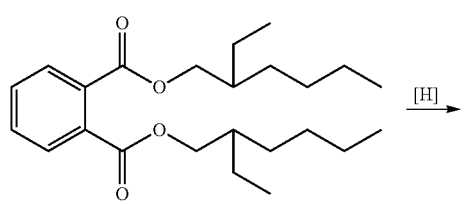

-continued

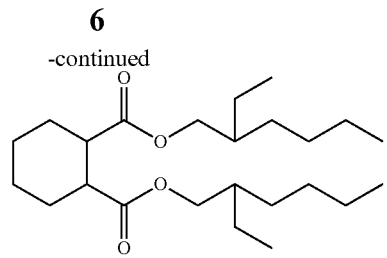

6 ml of catalyst A was placed in a fixed bed reactor (such as trickle bed reactor). A process for hydrogenation of the diisooctyl phthalate (DOP) was carried out in the trickle bed reactor according to scheme 3.

Hydrogenation reaction condition: at a normal pressure, the 2-ethyl-1-hexanol was used as a solvent, and the diisooctyl phthalate (DOP) and the solvent were supplied at a ratio of 1:1. The supply rate of the hydrogen was about 70 mL/min, the reaction temperature was about 200° C., and reaction flow rate was about 1.0 mL/hr.

FIG. 1A shows a diagram of the gas chromatography (GC) of diisooctyl phthalate (DOP). As shown in FIG. 1A, the signal of DOP was at 32.121 minutes, and a peak at 3.489 minutes was the signal of acetone (used as a diluent solvent).

Figure 1B:
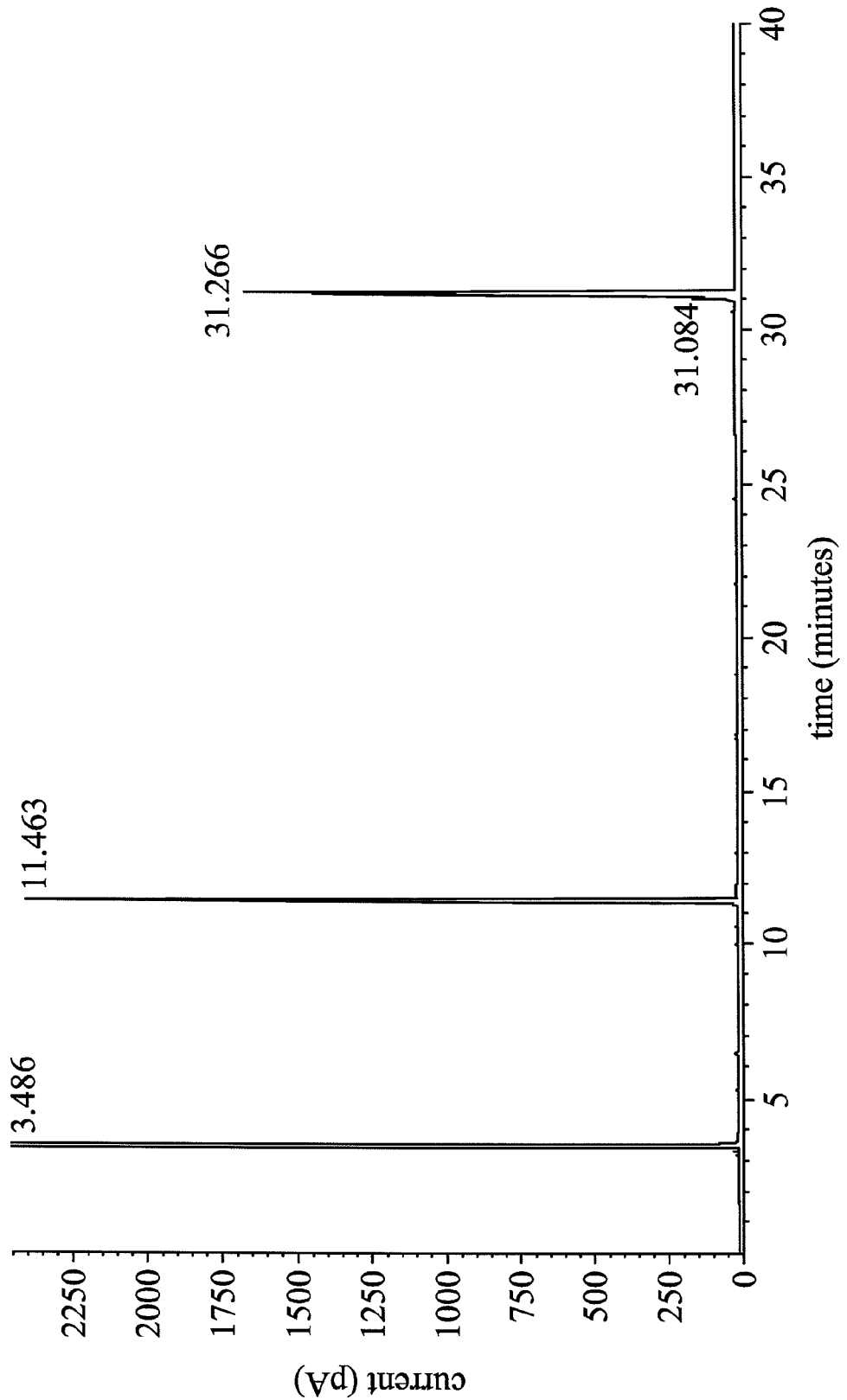

FIG. 1B shows a diagram of the gas chromatography (GC) of diisooctyl phthalate (DOP) after the hydrogenation reaction. The hydrogenated products (cis and trans) of the diisooctyl phthalate (DOP) were respectively at 31.084 minutes and 31.266 minutes. The signal of the 2-ethyl-1-hexanol was at 11.463 minutes and that of the acetone was at 3.486 minutes.

As shown in FIG. 1B, besides the hydrogenated product (cis and trans) of the diisooctyl phthalate (DOP), there were no other by-products presented. Thus, the data showed that about 100% of hydrogenation yield at a normal pressure was obtained.

Example 4

6 ml of catalyst B was placed in a fixed bed reactor (such as trickle bed reactor). A process for hydrogenation of the diisooctyl phthalate (DOP) was carried out in the trickle bed reactor according to scheme 3.

Hydrogenation reaction condition: the 2-ethyl-1-hexanol was used as a solvent, and the diisooctyl phthalate (DOP) and the solvent were supplied at a ratio of 1:1. The supply rate of the hydrogen was about 70 mL/min, the reaction temperature was about 200° C., the reaction pressure was about 10 Bar, and reaction flow rate was about 1.0 mL/hr. About 100% of hydrogenation yield was shown, following analysis by a gas chromatography (GC).

Example 5

6 ml of catalyst C was placed in a fixed bed reactor (such as trickle bed reactor). A process for hydrogenation of the diisooctyl phthalate (DOP) was carried out in the trickle bed reactor according to scheme 3.

Hydrogenation reaction condition: the 2-ethyl-1-hexanol was used as a solvent, and the diisooctyl phthalate (DOP) and the solvent were supplied at a ratio of 1:1. The supply rate of the hydrogen was about 70 mL/min, the reaction temperature was about 200° C., the reaction pressure was about 10 Bar, and reaction flow rate was about 1.5 mL/hr. About 100% of hydrogenation yield was shown, following analysis by a gas chromatography (GC).

Example 6

6 ml of catalyst C was placed in a fixed bed reactor (such as trickle bed reactor). A process for hydrogenation of the diisooctyl phthalate (DOP) was carried out in the trickle bed reactor according to scheme 3.

Hydrogenation reaction condition: at a normal pressure, the diisooctyl phthalate (DOP) was directly supplied into the reactor without any solvent. The supply rate of the hydrogen was about 70 mL/min, the reaction temperature was about 200° C. and the reaction flow rate was about 0.6 mL/hr. About 100% of hydrogenation yield was shown, following analysis by a gas chromatography (GC).

Example 7

6 ml of catalyst C was placed in a fixed bed reactor (such as trickle bed reactor). A process for hydrogenation of the diisooctyl phthalate (DOP) was carried out in the trickle bed reactor according to scheme 3.

Hydrogenation reaction condition: the diisooctyl phthalate (DOP) was directly supplied into the reactor without any solvent. The supply rate of the hydrogen was about 70 mL/min, the reaction temperature was about 200° C., and the pressure was about 10 Bar, and the reaction flow rate was about 2.5 mL/hr. About 100% of hydrogenation yield was shown, following analysis by a gas chromatography (GC).

Example 8

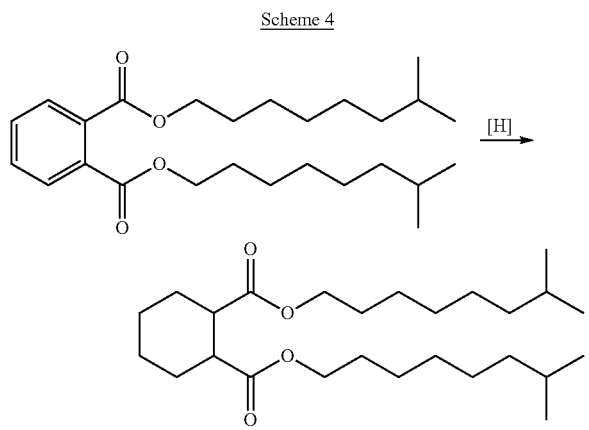

Scheme 4

6 ml of catalyst C was placed in a fixed bed reactor (such as trickle bed reactor). A process for hydrogenation of the diisononyl phthalate (DINP) was carried out in the trickle bed reactor according to scheme 4.

Hydrogenation reaction condition: at a normal pressure, isononyl alchol was used as a solvent, and the diisononyl phthalate and the solvent were supplied at a ratio of 1:1. The supply rate of the hydrogen was about 70 mL/min, the reaction temperature was about 200° C. and reaction flow rate was about 1.0 mL/hr. About larger than 99% of hydrogenation yield was shown, following analysis by a nuclear magnetic resonance spectroscopy (NMR).

Example 9

6 ml of catalyst C was placed in a fixed bed reactor (such as trickle bed reactor). A process for hydrogenation of the diisononyl phthalate (DINP) was carried out in the trickle bed reactor according to scheme 4.

Hydrogenation reaction condition: the isononyl alchol was used as a solvent, and the diisononyl phthalate and solvent was supplied at a ratio of 1:1. The supply rate of the hydrogen was about 70 mL/min, the reaction temperature was about 200° C., the reaction pressure was about 10 Bar and reaction flow rate was about 1.15 mL/hr. About larger than 99% of hydrogenation yield was shown, following analysis by a nuclear magnetic resonance spectroscopy (NMR).

Example 10

6 ml of catalyst C was placed in a fixed bed reactor (such as trickle bed reactor). A process for hydrogenation of the diisononyl phthalate (DINP) was carried out in the trickle bed reactor according to scheme 4.

Hydrogenation reaction condition: at a normal pressure, the diisononyl phthalate was directly supplied into the reactor without any solvent. The supply rate of the hydrogen was about 70 mL/min, the reaction temperature was about 200° C. and the reaction flow rate was about 0.54 mL/hr. About larger than 99% of hydrogenation yield was shown, following analysis by a nuclear magnetic resonance spectroscopy (NMR).

Example 11

6 ml of catalyst C was placed in a fixed bed reactor (such as trickle bed reactor). A process for hydrogenation of the diisononyl phthalate (DINP) was carried out in the trickle bed reactor according to scheme 4.

Hydrogenation reaction condition: the diisononyl phthalate was directly supplied into the reactor without any solvent. The supply rate of the hydrogen was about 70 mL/min, reaction temperature was about 200° C., the reaction pressure was about 10 Bar and the reaction flow rate was about 2.4 mL/hr. About larger than 99% of hydrogenation yield was shown, following analysis by a nuclear magnetic resonance spectroscopy (NMR).

While the disclosure has been described by way of example and in terms of the preferred embodiments, it is to be understood that the disclosure is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A process for hydrogenation of polycarboxylic acids or derivatives thereof, comprising:
   hydrogenation of polycarboxylic acids or derivatives thereof in the presence of a catalyst, wherein the catalyst comprise an active metal and a support, the support comprises a Group IIA element and a Group IIIA element, and the active metal comprises a Group VIIIB element.

2. The process for hydrogenation of polycarboxylic acids or derivatives thereof as claimed in claim 1, wherein the polycarboxylic acids comprise phthalic acids.

3. The process for hydrogenation of polycarboxylic acids or derivatives thereof as claimed in claim 1, wherein the polycarboxylic acids are selected from a group consisting of isophthalic acids, trimellitic acids, trimesic acids, hemimellitic acids or pyromellitic acids.

4. The process for hydrogenation of polycarboxylic acids or derivatives thereof as claimed in claim 1, wherein the polycarboxylic acids comprise terephthalic acids.

5. The process for hydrogenation of polycarboxylic acids or derivatives thereof as claimed in claim 1, wherein the polycarboxylic acid derivatives are selected from a group consisting of $C_1$-$C_{30}$ alkyl ester, $C_3$-$C_{30}$ cycloalkyl ester or $C_1$-$C_{30}$ alkoxyalkyl ester.

6. The process for hydrogenation of polycarboxylic acids or derivatives thereof as claimed in claim 1, wherein the polycarboxylic acids or derivatives thereof are selected from a group consisting of diethyl phthalate (DEP), dibutyl phthalate (DBP), diisooctyl phthalate (DOP) or diisononyl phthalate.

7. The process for hydrogenation of polycarboxylic acids or derivatives thereof as claimed in claim 1, wherein the catalyst further comprises an additive, and the additive comprises activated carbon, silicon carbide, aluminum oxide, silicon dioxide, titanium dioxide or combinations thereof.

8. The process for hydrogenation of polycarboxylic acids or derivatives thereof as claimed in claim 1, wherein the Group IIA element is selected from a group consisting of Mg, Ca, Sr, Ba or combinations thereof.

9. The process for hydrogenation of polycarboxylic acids or derivatives thereof as claimed in claim 1, wherein the Group IIIA element is selected from a group consisting of B, Al or combinations thereof.

10. The process for hydrogenation of polycarboxylic acids or derivatives thereof as claimed in claim 1, wherein the Group VIIIB element is selected from a group consisting of Pt, Pd, Ru, Rh or combinations thereof.

11. The process for hydrogenation of polycarboxylic acids or derivatives thereof as claimed in claim 1, wherein the active metal comprises 0.2-10 weight % of the catalyst.

12. The process for hydrogenation of polycarboxylic acids or derivatives thereof as claimed in claim 1, wherein the process for hydrogenation of polycarboxylic acids or derivatives thereof is carried out in a reactor, and the reactor comprises a batchwise reactor or trickle bed reactor.

13. The process for hydrogenation of polycarboxylic acids or derivatives thereof as claimed in claim 11, wherein the reaction is conducted at a pressure of about 1-50 Bar.

14. The process for hydrogenation of polycarboxylic acids or derivatives thereof as claimed in claim 11, wherein the reaction is conducted at a temperature of about 100-250° C.

* * * * *